United States Patent [19]
Benjamin

[11] Patent Number: 4,846,197
[45] Date of Patent: Jul. 11, 1989

[54] THERAPEUTIC DEVICE

[76] Inventor: Kenneth M. Benjamin, 3326 Woodbine St., #7, Los Angeles, Calif. 90064

[21] Appl. No.: 174,201

[22] Filed: Mar. 28, 1988

[51] Int. Cl.$^4$ ............................................. A61F 5/44
[52] U.S. Cl. ...................................... 128/844; 604/353
[58] Field of Search ................. 128/132 R, 79, 830, 128/842–844; 604/349, 350, 351, 352, 353, 330

[56] References Cited

U.S. PATENT DOCUMENTS

| | | | |
|---|---|---|---|
| 824,634 | 6/1906 | Ezell | 604/351 |
| 2,610,630 | 9/1952 | Crew | 604/347 |
| 3,759,254 | 9/1973 | Clark | 604/349 |
| 3,998,228 | 12/1976 | Poidomani | 604/351 |
| 4,074,712 | 2/1978 | Wright | 604/349 |
| 4,354,494 | 10/1982 | Hogin | 604/349 |
| 4,415,548 | 11/1983 | Reddy | 604/349 |

FOREIGN PATENT DOCUMENTS

| | | | |
|---|---|---|---|
| 0146306 | 6/1936 | Austria | 604/349 |
| 0211350 | 6/1909 | Fed. Rep. of Germany | 604/349 |
| 0254211 | 11/1912 | Fed. Rep. of Germany | 604/349 |
| 2020280 | 11/1971 | Fed. Rep. of Germany | 604/349 |
| 8605681 | 10/1986 | World Int. Prop. O. | 604/349 |

*Primary Examiner*—C. Fred Rosenbaum
*Assistant Examiner*—Mario Costantino
*Attorney, Agent, or Firm*—Roger A. Marrs

[57] ABSTRACT

A condom is disclosed herein having an elongated sleeve of substantially constant cross-section that terminates at one end in an expandable bulbous portion with a dimpled projection lying along the central longitudinal axis of the sleeve. An elastic retainer band is disposed on the opposite end of the sleeve while a narrower retainer band is integrally disposed between the sleeve and the bulbous portion. A marker is provided adjacent to the sleeve at the bulbous portion indicating the forward end intended to be rolled outwardly to advance the sleeve from its storage position to its elongated operative position.

2 Claims, 1 Drawing Sheet

THERAPEUTIC DEVICE

BACKGROUND OF THE INVENTION

1. Field of the Invention

The present invention relates to the field of therapeutic devices and more particularly to a novel condom having spaced-apart elastic bands for holding the condom in position and which may include several openings disposed between the bands so as to expose penile flesh when the condom is in its operative position.

2. Brief Description of the Prior Art

In the past, it has been the conventional practice to fabricate condoms as a single elongated, sleeve-like member of elastic material so that when in its operative position, the elasticity of the member will totally constrict to maintain the condom in position on the penile member. However, problems and difficulties have been encountered with conventional condoms which stem primarily from the fact that the penile member is entirely covered so that no portion of penile flesh or skin is exposed, resulting in a loss of feel and sensitivity during intercourse. Although it may be desirable to have all such penile portions covered for infectious disease prevention, the condom is used for other uses such as birth control among partners where transmittal of infectious diseases is not the main concern.

In such instances as the latter, it is desired that for full satisfaction, a maximum portion of penile skin be available or exposed during intercourse. Also, conventional condoms are known to become dislodged or inadvertently disassembled from the penile member during an intercourse procedure so that the desired effect of using a condom in the first place is lost. For retention, conventional condoms generally rely on the integral elasticity of the material composition to constrict about the penile member. However, the elasticity is very limited and is not properly distributed about the penile member for constriction at locations providing maximum retention.

Therefore, it is among the primary objects of the present invention to provide a novel condom which includes restrictive means by which the condom may be retained the penile member in a convenient and comfortable fashion and which may include relatively large openings in its integral construction to permit exposure of penile skin or flesh during an intercourse procedure.

Another object of the present invention is to provide a novel condom having improved retention means as well as providing large openings for exposing a substantial area of penile skin or flesh during the intercourse procedure.

Still a further object of the present invention is to provide a novel condom having indicator means effective for the user to install the condom on a penile member in a proper manner so that it may be deployed from a coiled or rolled condition to an expanded operative position.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

DESCRIPTION OF THE PREFERRED EMBODIMENT

Figure 1:
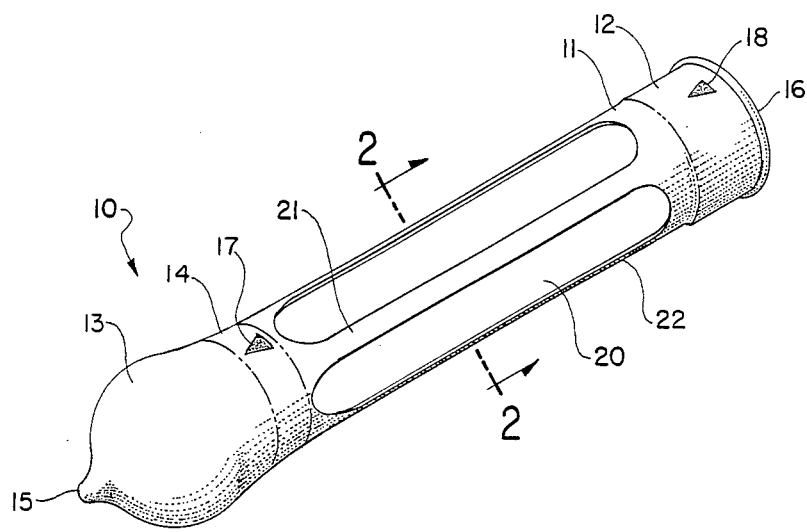
FIG. 1 is a perspective view of the novel condom illustrated in its expanded operative position incorporating the present invention.

Referring to FIG. 1, the novel condom of the present invention is illustrated in the general direction of arrow 10 which includes an elongated sleeve 11 having a band 12 at one end and a bulbous portion 13 integrally formed at its opposite end. The bulbous portion 13 is joined to the sleeve by means of a constrictive band 14 similar to the band 12 and in spaced relationship therewith. Preferably, the band 14 is of narrower width than the band 12; however, both bands are coaxially disposed about the central longitudinal axis of the sleeve 11.

The bulbous portion 13 serves as a closure for the sleeve 11 and includes a dimpled portion or reservoir 15 which is on the central longitudinal axis of the sleeve 11. In use, spermicide may be used within the bulbous portion 13 at the desire of the user. The opposite end of the sleeve 11 terminates in a folded roll of material, indicated by numeral 16, from which the sleeve is paid out when the device is being placed on a penile member. In its storage position, the sleeve, including the bulbous portion, is rolled about the rim 16 and in its operative position, as illustrated, the sleeve and bulbous portion are outwardly rolled.

As an aid to the user in properly placing the condom on a penile member and in deploying the sleeve in a proper direction, the inventive condom includes an indicator means taking the form of a visual nub 17 carried on the forward band 14. If desired, an additional indicator 18 may be provided on the rear band 12. The indicators may be visually observed by the user or may be felt by the fingers of the user in order to determine direction of deployment of the sleeve preparatory to placing the condom on the penile member.

In one form of the invention, substantial openings, such as indicated by numeral 20, are provided which define between adjacent ones of a plurality of straps, such as straps 21 and 22. The opposite ends of the plurality of straps are integrally joined with the sleeve 11 terminating in the bands 14 and 12 respectively. As illustrated, four straps are shown forming the major length of the sleeve 11 and the exposed areas 20 between adjacent ones of the straps provide sufficient exposure to penal skin area so that the user is afforded the beneficial effects of sensation during the intercourse procedure.

Figure 2:
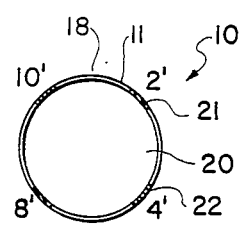
FIG. 2 is a transverse cross-sectional view of the condom shown in FIG. 1 taken in the direction of arrows 2—2 thereof.

As illustrated more clearly in FIG. 2, it is preferred that the plurality of straps be placed in a particular location with respect to the bands 12 and 14. For example, it is noted that the straps are arranged in a coaxial manner with respect to the bands and that the straps are located at clock positions, such as 2:00 o'clock, 4:00 o'clock, 8:00 o'clock and 10:00 o'clock respectively. These respective positions are noted by primes adjacent to the numerals representing the clock position.

Therefore, it can be seen that the condom of the present invention incorporates a variety of features which are new and novel over existing condoms. The condom is rolled for storage purposes in a conventional manner and may be unrolled into an operative position by using the indicators 17 or 18. Only one indicator is needed. Additionally, the straps, such as strap 21, provide an integral connection between the forward and rearward retaining straps 14 and 12 respectively so that a sleeve-like member 11 is defined with the enclosed end defining the bulbous portion 13. If desired, a spermicide may be used and, in addition to the retaining bands, an adhesive may be used on the inside of the bands for further retaining purposes. It is also to be noted that in one form of the invention, the diameter of the forward retaining band 14 may be of smaller measurement than the diameter of the rearward retaining band 12. Thus, greater adhesion or retention may occur since the base of the penile member is generally of greater diameter than the forward end. Therefore, the device of the present invention is more comfortable to the user than conventionally known condoms. In use, the forward retaining band 14 may reside immediately behind the glans penis while the bulbous portion 13 is forwardly projecting over the head of the penis.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A condom comprising the combination of:
an elongated stretchable member composed of resilient material having a cylindrical sleeve having a central longitudinal axis terminated at its opposite ends by a pair of radially constrictive bands;
a bulbous portion enclosing one end of said sleeve adjacent to a selected one of said bands;
said bands being coaxially disposed with respect to said sleeve and yieldably expandable radially when said sleeve is in an operative position to provide holding tension;
said sleeve capable of being rollable into a storage position;
marker means disposed externally on each of said sleeve bands in axial alignment and indicative of expansion from said storage position to said operative position;
said marker means including a physically raised element having an arrow shape pointing in the direction of and towards said bulbous portion;
said sleeve includes a plurality of elongated flexible strips extended between said bands coaxially disposed with respect to said central longitudinal axis of said sleeve;
said straps number at least four arranged clockwise at 2, 4, 8 and 10 clock locations with respect to a cross-sectional view of said sleeve so that substantial elongated openings are defined between adjacent straps at the top, opposite sides and bottom of said sleeve.

2. A condom comprising:
an elongated member composed of resilient material and capable of being adapted to be unrolled axially from a storage position to an operative position;
said member having radially yieldable constricting retaining means at its opposite ends to retain said member on a penile member said retaining means comprising at least one radially contractable band at each end of said member;
a bulbous end for enclosing the glans penis and expandably closing one end of said member said bulbous member integrally joined to one of said bands;
a plurality of open areas defined along the length of said member between adjacent straps which extend parallel to and coaxially with the central longitudinal axis of said member, said straps extending between said bands;
raised marker means disposed on said member on opposite ends thereof in linear alignment indicative of directional unrolling from said storage position to said operative position;
said retaining means includes said constrictive bands being of different diameters in their relaxed condition and spaced apart from each other by said straps.

* * * * *